United States Patent [19]

Stutz et al.

[11] Patent Number: 5,663,383
[45] Date of Patent: Sep. 2, 1997

[54] PROCESS FOR THE PREPARATION OF 3-HYDROXYOXETANES

[75] Inventors: Wolfgang Stutz, Münchwilen; Rudolf Waditschatka, Gipf-Oberfrick; Klas Winter, Massongex, all of Switzerland; Matthias von Frieling, Freiburg, Germany; Remy Gressly, Le Bouveret, Switzerland; Beat Jau, Aesch, Switzerland; Sebastien Bürki, Monthey, Switzerland

[73] Assignee: Ciba-Geigy Corporation, Tarrytown, N.Y.

[21] Appl. No.: 671,905

[22] Filed: Jun. 28, 1996

[30] Foreign Application Priority Data

Jun. 29, 1995 [CH] Switzerland ............... 1913/95

[51] Int. Cl.$^6$ ................. C07D 305/08
[52] U.S. Cl. ................. 549/510; 546/281.7
[58] Field of Search ................. 549/510

[56] References Cited

U.S. PATENT DOCUMENTS

| | | | |
|---|---|---|---|
| 4,009,182 | 2/1977 | Ardis et al. | 260/333 |
| 4,395,561 | 7/1983 | Baum et al. | 549/420 |
| 5,209,771 | 5/1993 | Meyer | 504/178 |
| 5,342,823 | 8/1994 | Kühlmeyer et al. | |
| 5,489,695 | 2/1996 | Meyer | 549/510 |

OTHER PUBLICATIONS

J. Org. Chem., 1983, vol. 48, No. 18, pp. 2953–2956.
J. Org. Chem., 1973, vol. 38, No. 11, pp. 2061–2066.
J. Org. Chem., 1981, vol. 46, No. 2, pp. 306–311.

*Primary Examiner*—Bernard Dentz
*Attorney, Agent, or Firm*—William A. Teoli, Jr.

[57] ABSTRACT

A process for the preparation of 3-hydroxyoxetanes of formula I

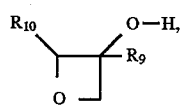
(I)

wherein $R_9$ and $R_{10}$ are each independently of the other hydrogen or $C_1$–$C_4$alkyl, by (1) reaction of a carboxylic acid R—$CO_2$H, wherein R is branched alkyl, with an epichlorohydrin of formula II

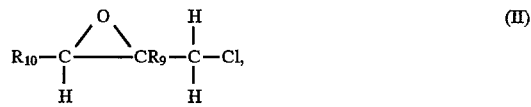
(II)

wherein $R_9$ and $R_{10}$ are as defined hereinbefore, to form an ester of formula III

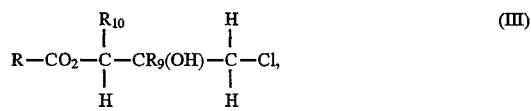
(III)

wherein R, $R_9$ and $R_{10}$ are as defined hereinbefore, (2) reaction of that ester with an ether of formula IV $$CHR_1=CH-O-R_2 \qquad (IV),$$

wherein $R_1$ is hydrogen or methyl, $R_2$ is $C_1$–$C_6$alkyl, or $R_1$ and $R_2$ together form a radical of formula —$(CH_2)_3$—, in the presence of a catalyst, to form an ester of formula V

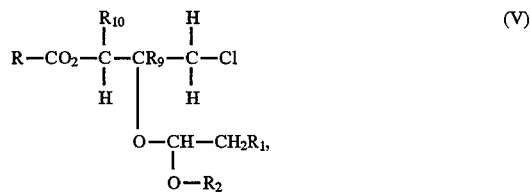
(V)

(3) hydrolysis and cyclization of that ester in the presence of a base to form a compound of formula VI

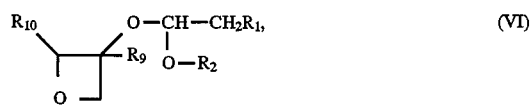
(VI)

wherein $R_1$, $R_2$, $R_9$ and $R_{10}$ are as defined hereinbefore, (4) acetal cleavage in the presence of an acid to form the corresponding 3-hydroxyoxetane and (5) isolation of that 3-hydroxyoxetane.

29 Claims, No Drawings

PROCESS FOR THE PREPARATION OF 3-HYDROXYOXETANES

The present invention relates to a novel process for the preparation of 3-hydroxyoxetanes.

U.S. Pat. No. 4,395,561 describes a process for the preparation of 3-hydroxyoxetane. In accordance with that process, carboxylic acids of the formula $CH_3(CH_2)_nCO_2H$, wherein n is 0, 1, 2 or 3, are used as starting materials and are reacted in the presence of $FeCl_3$ with epichlorohydrin to form an ester of the formula $CH_3(CH_2)_nCO$—O—$CH_2CH$(OH)$CH_2$—Cl. That ester is cyclised by basic hydrolysis to form an oxetane, after the hydroxy group of the ester has been protected by a group that is resistant to the action of bases. After the hydrolysis and cyclisation, that protecting group is removed by reaction with an acid. The resulting 3-hydroxyoxetane is then isolated by extraction and/or distillation.

Surprisingly, it has now been found that that process can be improved significantly by using carboxylic acids of the formula R—$CO_2H$ wherein R is branched alkyl instead of the mentioned unbranched carboxylic acids of formula $CH_3(CH_2)_nCO_2H$.

The present invention thus relates to a process for the preparation of 3-hydroxyoxetanes of formula I

wherein $R_9$ and $R_{10}$ are each independently of the other hydrogen or $C_1$-$C_4$alkyl, by (1) reaction of a carboxylic acid R—$CO_2H$, wherein R is branched alkyl, with an epichlorohydrin of formula II

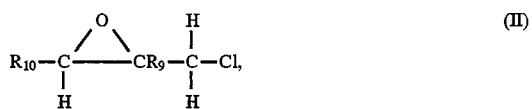

wherein $R_9$ and $R_{10}$ are as defined hereinbefore, to form an ester of formula III

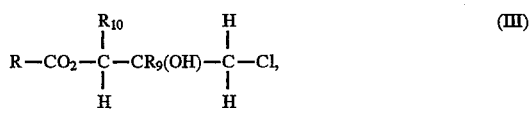

wherein R, $R_9$ and $R_{10}$ are as defined hereinbefore, (2) reaction of that ester with an ether of formula IV $$CHR_1=CH-O-R_2 \qquad (IV),$$

wherein $R_1$ is hydrogen or methyl, $R_2$ is $C_1$-$C_6$alkyl, or $R_1$ and $R_2$ together form a radical of formula —$(CH_2)_3$—, in the presence of a catalyst, to form an ester of formula V

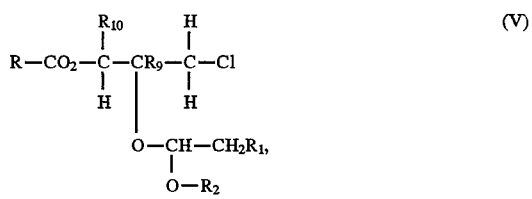

(3) hydrolysis and cyclisation of that ester in the presence of a base to form a compound of formula VI

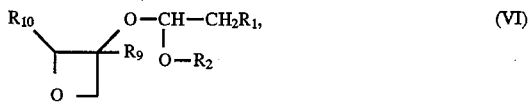

wherein $R_1$, $R_2$, $R_9$ and $R_{10}$ are as defined hereinbefore, (4) acetal cleavage in the presence of an acid to form the corresponding 3-hydroxyoxetane and (5) isolation of that 3-hydroxyoxetane.

In Step (1) of the process according to the invention, those carboxylic acids R—$CO_2H$ wherein the alkyl radical R has a branch at the α-carbon atom are preferably used. R is especially an α-branched alkyl radical having from 3 to 8 carbon atoms, of which, for example 1-ethylpentyl and t-butyl and, especially, 1-ethylpropyl are particularly suitable.

Acids having cyclic alkyl radicals, such as cyclopentyl, cyclohexyl and cyclooctyl, may also be used with advantage in the process according to the invention.

Preferably, the addition of the carboxylic acid to the epichlorohydrin is carried out in the presence of a catalyst, which may be either acidic or basic. Suitable acidic catalysts are, for example, Lewis acids, such as $FeCl_3$ mentioned in U.S. Pat. No. 4,395,561, acidic powdered minerals, such as montmorillonite, and also the conventional mineral acids, such as hydrochloric, hydrobromic, phosphoric, nitric and sulfuric acid. Phase transfer catalysts are also suitable for the first reaction Step. Tetrabutylammonium chloride, 3-(1-pyridino)-1-propane sulfonate and pyridine tosylate may be mentioned as examples thereof. The process according to the invention is, however, advantageously carried out in the presence of a basic catalyst. Alkali metal hydroxides, for example, such as sodium and potassium hydroxide, may be used, but trialkylamines, such as triethyl- and tributyl-amine, N,N-dialkylanilines, such as N,N-diethylaniline, and substituted pyridines, especially pyridines substituted by alkyl- or dialkyl-amino groups, for example 2-methyl- and 2,6-dimethyl-pyridine and also N,N-dimethylaminopyridine, are especially suitable. The most favourable results are obtained with pyridine itself. It is furthermore also possible to use polycyclic, especially bicyclic, amidines, such as DBU and DBN, which are described, for example, in Synthesis, 591, 1972, and especially also polymer-bonded pyridines and alkylated aminopyridines, such as poly-DMAP.

Vinyl ether derivatives of formula IV have proved especially suitable for the introduction of the protecting group in Step (2). The substituent $R_2$ in formula IV is, for example, methyl, ethyl, propyl, butyl, pentyl or hexyl or a branched isomer thereof. Furthermore, $R_2$ together with $R_1$ may form a —$(CH_2)_3$— radical and thus form a dihydropyrane ring. Vinyl ethers especially suitable for use in the process according to the invention are those wherein $R_1$ is hydrogen and $R_2$ is $C_2$-$C_5$alkyl, such as, for example, ethyl, butyl, pentyl, and especially isobutyl, vinyl ethers, and also methylisopropenyl ether.

The reaction of the ester of formula III with the vinyl ether of formula IV in Step (2) is carried out in the presence of a catalyst. There are suitable for that purpose especially alkyl- and aryl-sulfonic acids and their salts. Methanesulfonic acid and p-toluenesulfonic acid may be mentioned as preferred examples, but good results are also obtained with halogenated carboxylic acids, such as trifluoro- and trichloro-acetic acid and also with the above-mentioned mineral acids, especially if those acids are anhydrous. Acidic ion exchange resins, such as Dowex®, may also be used.

The hydrolysis and cyclisation of the protected ester of formula V to form the protected 3-hydroxyoxetane in Step (3) is carried out in alkaline medium. There may be chosen as base in principle any compound that can release hydroxyl ions into solvents, especially polar solvents, especially sodium and potassium hydroxide and also corresponding methanolates. Preferred polar solvents are, for example, alcohols, DMF, DMA, N-methyl-pyrrolidone, dioxane and, especially, water.

The removal of the protecting group in Step (4), an acetal cleavage, is achieved by reacting the protected 3-hydroxyoxetane with an acid in a protic solvent, such as an alcohol and especially water. There are suitable, for example, the acids mentioned above for use in Step (2), mineral acids, such as hydrochloric, hydrobromic, sulfuric, nitric and phosphoric acid, assuming special importance. Sulfuric and hydrochloric acid are more especially preferred. After the acetal cleavage the reaction mixture may, especially when the reaction is carried out in batches, be neutralised with bases, such as, for example, alkali metal or alkaline earth metal hydroxides.

The process according to the invention can be carried out either in batches (discontinuously) or continuously.

The batchwise process is carried out preferably in conventional stirred vessels and also, in respect of the last Step, in conventional packed columns. In one variant of the batchwise process according to the invention, reaction Steps (1), (2) and (3) may be combined as a one-pot reaction, and the reaction product of Step (3), the protected 3-hydroxyoxetane of formula (VI), may be concentrated by azeotropic distillation or steam distillation.

The continuous process is preferred. In the continuous process a loop-type reactor is preferably used for carrying out Step (1). As a result, uniform distribution of the heat of reaction is ensured throughout the reactor, and the turbulent flow makes it possible for a high reflux ratio to be established. In order to achieve a high degree of conversion, a tubular reactor may be connected in series downstream of the loop-type reactor. The loop-type reactor is operated preferably at temperatures of from 90° to 130° C. The mean residence time is in that case in the range of from 40 to 60 minutes. The operating temperature of the downstream series-connected tubular reactor is usually somewhat higher, for example from 110° to 130° C., and the mean residence time therein is approximately from 10 to 20 minutes. Under those conditions yields of about 80% of compound of formula III are usually achieved in Step (1). The introduction of the protecting group in Step (2) is carried out preferably in a stirred vessel, since especially thorough mixing of the reaction mass is necessary. With reaction temperatures of from 40° to 55° C. and mean residence times of from 15 to 25 minutes, the compounds of formula V can be obtained in yields of about 95%. A multi-chamber reactor has proved advantageous for carrying out Step (3). Preferably, temperatures of from 140° to 150° C., which can be achieved at a pressure of approximately from 3 to 4 bar, are selected. At those temperatures, in order to be able to operate above the saturation pressure of the reaction mass a nitrogen cushion is preferably superimposed with which a total pressure of approximately 5 bar is established in the reactor. The mean residence time of the reaction mass in the reactor is usually from 50 to 70 minutes. By means of steam distillation the compound of formula VI can be concentrated to an approximately 80% strength aqueous solution. For the steam distillation there is advantageously used a column having baffles, for example cone/funnel baffles, or a stirred vessel cascade consisting, for example, of 3 stirred vessels, through which steam is conveyed below the surface in countercurrent. In that manner compounds of formula VI can be obtained in yields of more than 85%. The yields over all 3 Steps are thus usually in the range of from 64 to 70%. Cleavage of the compounds of formula VI to form the corresponding 3-hydroxyoxetanes in Step (4) can be carried out, for example, in a stirred vessel or in a stirred vessel cascade comprising approximately 2 stirred vessels. The reaction temperatures should in that case be in the range of from 50° to 70° C. and the mean residence times should be approximately from 1.5 to 3 hours per vessel (from 3 to 6 hours total residence time). Preferably, excess pressure, for example from 0.2 to 0.5 bar, is used in order to remove from the reaction mixture the acetaldehyde formed during the cleavage and at least partially also isobutanol and other low-boiling by-products present in low concentration. The 3-hydroxyoxetanes are obtained in the form of a substantially aqueous solution having a 3-hyhdroxyoxetane content of approximately 15 to 25%. The yields are generally from 90 to 95%. Purification of the 3-hydroxyoxetanes is effected in Step (5) preferably by rectification of the said aqueous solution of crude product from Step (4). It is advantageous to distil off the readily volatile components, such as water and alcohols (corresponding to the meanings of $R_1$ und $R_2$), especially isobutanol, from the head of a first column at reduced pressure, for example 100 mbar. The bottom product can then be fed into a second column where separation into high-boiling by-products and 3-hydroxyoxetane (head product) is carried out. In that way 3-hydroxyoxetanes can be obtained in purities of more than 95% and in yields of 95% and above.

The yield of 3-hydroxyoxetanes over all Steps is from 60 to 66%.

In one variant of the continuous process according to the invention, the rectification may be preceded by an extraction for the purpose of obtaining a product solution having a significantly reduced salt content. The extraction agent used is preferably the solvent already present (corresponding to the radicals $R_1$ and $R_2$) in the product solution, especially isobutanol. It is obtained continuously during the phase separation of the head product in the first column. The extraction may be carried out in any customary extraction apparatus, but is preferably carried out in a multi-stage stirred extraction column.

The process according to the invention by means of which preferably unsubstituted 3-hydroxyoxetanes are prepared has the following advantages over the process disclosed in U.S. Pat. No. 4,395,561:

Yield, which can be increased by at least 40 to 65% or more compared with the process according to U.S. Pat. No. 4,395,561 (47%); the increase in yield in Step (3), which deserves special mention, is attributable mainly to the use of branched carboxylic acids;

the isomer ratio of compound of formula III to compound of formula IIIa

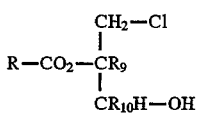

(IIIa)

at the end of Step (1) distinctly favours the compound of formula III, which increases the yield and the purity of the product;

- purity of the product, which may amount to 95% or more;
- efficiency of the process, which can be increased by a substantial shortening of the reaction times;
- process safety, especially in continuous operation, where it is possible to operate with reaction vessels that are 20 times smaller, that is to say with smaller amounts of reaction mixture, to obtain the same amount of product as in batchwise operation; the consequences in the case of an incident are thus substantially reduced. It should also be taken into account that especially the distillative purification in Step (5) is carried out at temperatures of from 130° to 150° C., at which thermal decomposition of the 3-hydroxyoxetane can take place in as little as 4 hours. Carrying out the process batchwise is in that case a disadvantage in view of high residence times;
- reproducible quality of the product, especially in the case of continuous operation, where process parameters, once set, remain constant until the plant is turned off. In the case of batchwise operation it is possible that even slightly modified parameters may lead to different product qualities;
- the recyclability of branched carboxylic acids is substantially better than that of unbranched.

The 3-hydroxyoxetanes prepared in accordance with the invention are used specifically as starting materials in the preparation of sulfonylurea herbicides as described, for example, in U.S. Pat. No. 5,209,771 and U.S. Pat. No. 5,342,823. In a first step, 3-hydroxyoxetane prepared in accordance with the invention is reacted, for example, with an acid chloride of formula VIII Q-COCl  (VIII), wherein Q is a radical of the formula

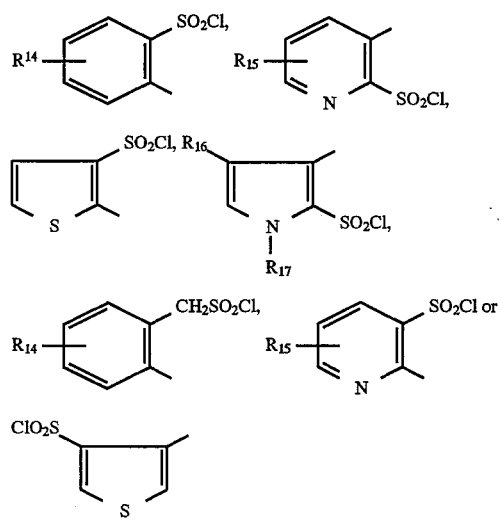

wherein $R_{14}$ is hydrogen, fluorine, chlorine, bromine, iodine or $-(X)_nR_3$ wherein X is oxygen, sulfur, SO or $SO_2$, $R_3$ is $C_1-C_4$alkyl, $C_1-C_4$alkyl substituted by from 1 to 4 halogen atoms, $C_1-C_3$alkoxy or by $C_1-C_3$alkylthio, or $R_3$ is $C_2-C_4$alkenyl or $C_2-C_4$alkenyl substituted by from 1 to 4 halogen atoms, and n is 0 or 1; or $R_{14}$ is nitro, $NR_4R_5$ wherein $R_4$ is hydrogen, methoxy, ethoxy or $C_1-C_3$alkyl and $R_5$ is hydrogen or $C_1-C_3$alkyl; or $R_{14}$ is $-CCR_6$ wherein $R_6$ is hydrogen, methyl or ethyl; or $R_{14}$ is $-O-CHR_7-CCR_6$ wherein $R_6$ is hydrogen, methyl or ethyl and $R_7$ is hydrogen or methyl; or $R_{14}$ is cyano, $R_{15}$ is hydrogen, fluorine, chlorine, $C_1-C_4$alkyl or methoxy, $R_{16}$ is hydrogen, fluorine or chlorine and $R_{17}$ is methyl or 2-pyridyl, to yield a compound of formula VII

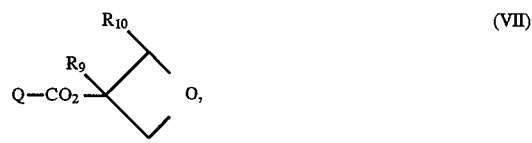

(VII)

wherein $R_9$ and $R_{10}$ are as defined hereinbefore, which then, as intermediate, can be converted into the corresponding sulfonylurea herbicide by methods that are customary and are described in U.S. Pat. No. 5,209,771 and U.S. Pat. No. 5,342,823, such as conversion into the corresponding sulfonamide and further reaction with a pyridyl-, pyrimidyl-, triazolyl- or triazinyl-phenylcarbamate or a pyridyl-, pyrimidyl-, triazolyl- or triazinyl-isocyanate.

In order to increase the purity of the sulfonylurea herbicides thus obtainable, the inventively prepared 3-hydroxyoxetanes can be treated directly before their reaction with the acid chloride of formula VIII with catalytic amounts of a preferably bivalent metal salt, in particular a chloride such as magnesium or calcium chloride.

With the 3-hydroxyoxetanes prepared in accordance with the invention, preferably the intermediates of formula VIIa

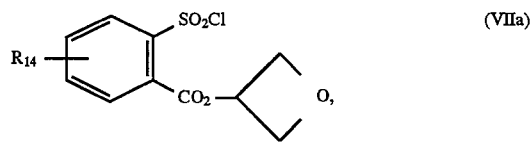

(VIIa)

wherein $R_{14}$ is as defined hereinbefore, and especially of formula VIIb

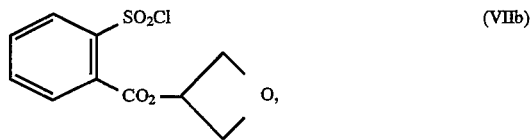

(VIIb)

are obtainable.

The Following Examples Further Illustrate the Invention

EXAMPLE 1

Batchwise Preparation of 3-hydroxyoxetane

Step (1): 296 g of epichlorohydrin are added dropwise at from 96° to 100° C., in the course of 4 hours, to a mixture of 2.53 g of pyridine and 383 g of 2-ethylbutyric acid in a 750 ml sulfonating flask. The mixture is then further reacted for 1 hour at that temperature, the temperature is reduced within a period of 3 hours to from 73° to 76° C. and the reaction mixture is left at that temperature for a further 2 hours. The ratio, determined by gas chromatography, of compound of formula III to compound of formula IIIa, wherein $R_9$ and $R_{10}$ are hydrogen and R is 1-ethylpropyl, is 91:9.

Step (2): 353 g of isobutyl vinyl ether are added dropwise at from 68° to 71° C.; in the course of 5 hours, to the reaction mixture from Step (1) and 5.23 g of methanesulfonic acid in a 1.5 l sulfonating flask. The mixture is then left at that temperature for 3 hours to complete the reaction.

Step(3): The reaction mixture from Step (2) is added dropwise at from 110° to 120° C., in the course of 4 hours, to a mixture of 736 g of an aqueous 40% sodium hydroxide solution and 10 g of 2-ethylbutyric acid in a 2.5 l sulfonating flask. By means of azeotropic distillation, continuous replacement of the water removed from the reaction mixture and removal of the aqueous phase in the distillate, 475 g of organic phase having an isobutoxy-ethoxy-oxetane content of 77.9% are obtained.

Step (4): 10% sulfuric acid is added dropwise at from 20° to 25° C. to a mixture of 446 g of isobutoxy-ethoxy-oxetane obtained in Step (3) and 400 g of water in a 1.5 l sulfonating flask until a pH value of from 2.5 to 3 is established. Acetaldehyde is then removed from the reaction mixture by evacuation to 300 mbar and heating to from 65° to 70° C. Then, either the pH value can be adjusted to from 8.5 to 9.0 by metering in 25% potassium hydroxide solution, the reaction mixture left at from 65° to 70° C. for 1 hour, then cooled to from 20° to 25° C. and adjusted to a pH value of from 7 to 7.5 with sulfuric acid, or the reaction mixture can be left to cool to from 20° to 25° C. and the pH value then adjusted to 7 by the addition of magnesium or calcium hydroxide solution.

Step (5): Water and low-boiling organic by-products are removed from the reaction mixture from Step (4) by means of fractional distillation over a packed column. The residue remaining is distilled by means of a molecular distillation apparatus, yielding 146 g of 3-hydroxyoxetane (96%).

The yield of 3-hydroxyoxetane over all Steps is 63%.

EXAMPLE 2

Batchwise Preparation of 3-Hydroxyoxetane

Step (1): 485.6 g of epichlorohydrin are added dropwise at from 80° to 85° C., in the course of 3.5 hours, to a mixture of 8.1 g of anhydrous iron(III) chloride and 592.8 g of 2-ethylbutyric acid in a 2.5 l sulfonating flask. The mixture is then further reacted at that temperature for 2 hours. The ratio, determined by gas chromatography, of compound of formula III to compound of formula IIIa, wherein $R_9$ and $R_{10}$ are hydrogen and R is 1-ethylpropyl, is 93:7.

Step (2): 551 g of isobutyl vinyl ether are added dropwise at from 68° to 71° C., in the course of 5 hours, to the reaction mixture from Step (1) and 3.7 g of methanesulfonic acid in a 2.5 l sulfonating flask. The mixture is then left at that temperature for 3 hours to complete the reaction. The conversion in this Step is more than 96%.

Step (3): The reaction mixture from Step (2) is added dropwise at from 110° to 120° C., in the course of 4 hours, to a mixture of 1150 g of an aqueous 40% sodium hydroxide solution and 15 g of 2-ethylbutyric acid in a 4.5 l sulfonating flask. By means of azeotropic distillation, continuous replacement of the water removed from the reaction mixture and removal of the aqueous phase in the distillate, 816 g of organic phase having an isobutoxy-ethoxy-oxetane content of 82% are obtained.

Step (4): A mixture of 776 g of isobutoxy-ethoxy-oxetane obtained in Step (3) and 700 g of water is reacted as described in Example 1, Step (4).

Step (5): Water and low-boiling organic by-products are removed from the reaction mixture from Step (4) by means of fractional distillation over a packed column. The residue remaining is distilled by means of a molecular distillation apparatus, yielding 258 g of 3-hydroxyoxetane (96.2%).

The yield of 3-hydroxyoxetane over all Steps is 70.5%.

EXAMPLE 3

Batchwise Preparation of 3-Hydroxy-3-methyl-oxetane

Step (1): 27.7 g of 2-chloromethyl-2-methyl-oxirane are added dropwise at from 80° to 85° C., in the course of 4 hours, to a mixture of 0.42 g of anhydrous iron(III) chloride and 29.3 g of 2-ethylbutyric acid in a 100 ml sulfonating flask. The mixture is then further reacted for 27 hours at that temperature.

Step (2): 27.5 g of isobutyl vinyl ether are added dropwise at from 68° to 72° C., in the course of 4 hours, to the reaction mixture from Step (1) and 0.147 g of methanesulfonic acid. The mixture is then left at that temperature for 16 hours to complete the reaction.

Step (3): The reaction mixture from Step (2) is added dropwise at from 110° to 120° C., in the course of 3 hours, to 57.5 g of an aqueous 40% sodium hydroxide solution. By means of azeotropic distillation, continuous replacement of the water removed from the reaction mixture and removal of the aqueous phase in the distillate, 35.4 g of organic phase having an isobutoxy-ethoxy-methyl-oxetane content of 47.5% are obtained, corresponding to a yield of 35.7%.

Step (4): 10% sulfuric acid is added dropwise at from 20° to 25° C. to a mixture of 35.4 g of isobutoxy-ethoxy-methyl-oxetane obtained in Step (3) and 27.5 g of water until a pH value of from 2.5 to 3 is established. Acetaldehyde is then removed from the reaction mixture by evacuation to 300 mbar and heating to from 50° to 70° C. The pH value is adjusted to from 8.5 to 9.0 by metering in 25% potassium hydroxide solution, and the reaction mixture is left at from 65° to 70° C. for 1 hour, then cooled to from 20° to 25° C. and adjusted to a pH value of from 7 to 7.5 with sulfuric acid.

Step (5): Water and low-boiling organic by-products are removed from the reaction mixture from Step (4) by means of fractional distillation over a packed column. The residue remaining, which is 9.5 g, has a 61% content of the title compound. The yield of 3-hydroxy-3-methyl-oxetane over all Steps is 26.4%.

EXAMPLE 4

Continuous Preparation of 3-Hydroxyoxetane

Step (1): In a 3.4 l loop-type reactor, 2-ethylbutyric acid and epichlorohydrin in excess (25 mol %) and also 1.5 mol % of pyridine (based on 2-ethylbutyric acid) are reacted with one another at a temperature of from 95° to 105° C. after a mean residence time of 45 minutes, the reaction mixture is introduced into a tubular reactor (cross-section: 38 mm, effective length: 1200 mm, nature of the packing material: Sulzer BX). The operating temperature in that reactor is from 110° to 120° C., and the mean residence time is 15 minutes. Excess epichlorohydrin is removed at 105° C. and 200 mbar. The chlorohydrin ester is obtained in a yield of 80%.

Step (2): The reaction mixture from Step (1) is introduced into a continuously operated 2.5 l stirred vessel and is reacted therein at a temperature of 43° C. with isobutyl vinyl ether (1.08 equivalents based on 2-ethylbutyric acid). At the same time methanesulfonic acid is added in an amount of 0.024 equivalents based on isobutyl vinyl ether. The mean residence time is 20 minutes. In this Step the stirring in very important since a fine white precipitate, which consists for the most part of pyridinium salt, is continuously formed during the reaction. Based on the ester used, the product is obtained in a 95% yield.

Step (3): This Step, hydrolysis and cyclisation, is carried out in a 10 l multi-chamber reactor at a temperature of 145° C. and a pressure of from 3 to 5 bar. 2.5 equivalents of sodium hydroxide solution in the form of a 35% strength aqueous solution heated to 145° C. are added. The residence times in the reactor are from 60 to 80 minutes. The product is removed from the reaction mixture by steam distillation. For that purpose, the reaction mixture is conveyed through a stirred vessel cascade, each vessel having a volume of 5 l, and from 2 to 2.5 kg of steam/kilo of reaction mixture from Step (3) are introduced in countercurrent below the surface. The product of this Step is obtained in a yield of 88%.

Step (4): The product of Step (3) (2.18 kg/hour) and water (1.35 kg/hour) are continuously metered into a reactor cascade consisting of two 10 l reactors under a pressure of 0.3 bar, at a temperature of 60° C. and with a mean residence time of from 4 to 5 hours (total), during the course of which the pH value is established at 3.0 with hydrochloric acid. The solution flowing out of the second stirred vessel is adjusted to a pH value of from 7 to 8 with sodium hydroxide solution. The yield of Step (4) product is 95%.

Step (5): The reaction solution obtained at the end of Step (4) is worked up by rectification on 2 columns. In the first column, at a head temperature of 40° C. and 100 mbar head pressure, all substances having a boiling point lower than that of 3-hydroxyoxetane are removed as head product (mainly isobutanol and water). The 3-hydroxyoxetane is fed at 130° C. into the second column together with the higher-boiling components and, at 10 mbar head pressure and 73° C. head temperature, is obtained as head product in a degree of purity greater than 95%.

The total yield of 3-hydroxyoxetane over all Steps is 60.5%.

EXAMPLE 5

Preparation of the Compound of Formula VIIb 109.6 g of o-sulfobenzoic acid monoammonium salt, obtainable by acidic ring opening of saccharin, are placed in 500 ml of toluene and 10 ml of DMF. In the course of 2 hours, 130 g of phosgene are introduced at a temperature of from 70° to 75° C. The mixture is then stirred for 30 minutes at that temperature and the temperature is subsequently increased, within a period of 1 hour, to from 105° to 110° C., the reaction mixture being maintained at that temperature for approximately 1 further hour until the evolution of gas has ceased. The mixture is allowed to cool to room temperature under a stream of nitrogen. Filtration is carried out and the residue is washed with toluene. The filtrate is fully concentrated by evaporation, and 120.4 g of o-sulfonic acid-benzoic acid dichloride are obtained in the form of a yellow oil. 34 g of that compound and 120.4 g of 3-hydroxyoxetane, optionally treated with catalytic amounts of magnesium chloride, are placed in 350 ml of methylene chloride at −5° C. 34 g of pyridine are then added dropwise thereto, the temperature not exceeding 0° C. After the dropwise addition, the reaction mixture is allowed to warm up to room temperature and is stirred for a further hour, a suspension being formed, to which ice-water is added. The organic phase is removed, washed with ice-water, cold sodium hydrogen carbonate solution and again with ice-water, and then dried over sodium sulfate and filtered. The compound of formula VIIb is obtained in a yield of 70%.

What is claimed is:

1. A process for the preparation of 3-hydroxyoxetanes of formula I

wherein $R_9$ and $R_{10}$ are each independently of the other hydrogen or $C_1$–$C_4$alkyl, by (1) reaction of a carboxylic acid R—$CO_2$H, wherein R is branched alkyl, with an epichlorohydrin of formula II

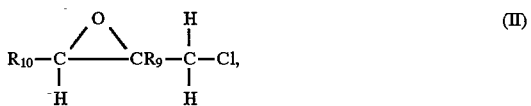

wherein $R_9$ and $R_{10}$ are as defined hereinbefore, to form an ester of formula III

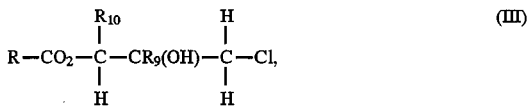

wherein R, $R_9$ and $R_{10}$ are as defined hereinbefore, (2) reaction of that ester with an ether of formula IV

wherein $R_1$ is hydrogen or methyl, $R_2$ is $C_1$–$C_6$alkyl, or $R_1$ and $R_2$ together form a radical of formula —$(CH_2)_3$—, in the presence of a catalyst, to form an ester of formula V

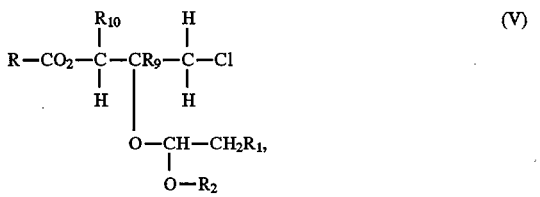

(3) hydrolysis and cyclisation of that ester in the presence of a base to form a compound of formula VI

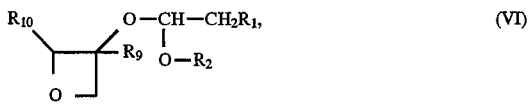

wherein $R_1$, $R_2$, $R_9$ and $R_{10}$ are as defined hereinbefore, (4) acetal cleavage in the presence of an acid to form the corresponding 3-hydroxyoxetane and (5) isolation of that 3-hydroxyoxetane.

2. A process according to claim 1, wherein there is used as carboxylic acid in Step (1) one in which R is α-branched alkyl.

3. A process according to claim 2, wherein there is used as carboxylic acid one in which R is α-branched $C_3$–$C_8$alkyl.

4. A process according to claim 3, wherein there is used as carboxylic acid one in which R is 1-ethylpropyl, 1-ethylpentyl or t-butyl.

5. A process according to claim 1, wherein in Step (1) an acidic or basic catalyst is used.

6. A process according to claim 5, wherein there is used as acidic catalyst a Lewis acid.

7. A process according to claim 6, wherein there is used as acidic catalyst iron(III) chloride.

8. A process according to claim 5, wherein there is used as basic catalyst pyridine, a pyridine substituted by alkyl- or dialkyl-amino groups, a trialkylamine or a polymer-bonded pyridine or a polymer-bonded alkylated aminopyridine.

9. A process according to claim 8, wherein pyridine is used as basic catalyst.

10. A process according to claim 1, wherein there is used in Step (2) an ether in which $R_1$ is hydrogen and $R_2$ is $C_3$-$C_5$alkyl.

11. A process according to claim 10, wherein $R_2$ is isobutyl.

12. A process according to claim 1, wherein there is used as catalyst in Step (2) p-toluenesulfonic acid or methanesulfonic acid.

13. A process according to claim 1, wherein there is used as base in Step (3) sodium or potassium hydroxide.

14. A process according to claim 1, wherein in Step (3) the hydrolysis and cyclisation of the ester are carried out in the presence of a base in a polar solvent.

15. A process according to claim 14, wherein water is used as polar solvent.

16. A process according to claim 1, wherein the compound of formula VI formed in Step (3) is, before acetal cleavage in Step (4), concentrated by azeotropic distillation or by steam distillation.

17. A process according to claim 1, wherein there is used as acid in Step (4) a mineral acid in a protic solvent.

18. A process according to claim 17, wherein there is used as acid in Step (4) sulfuric or hydrochloric acid.

19. A process according to claim 1, wherein after the acetal cleavage in Step (4) the reaction mixture is neutralised with a base.

20. A process according to claim 19, wherein neutralisation is effected with an alkali metal or alkaline earth metal hydroxide.

21. A process according to claim 1, wherein a rectification is carried out in Step (5).

22. A process according to claim 21, wherein an extraction is carried out before the rectification.

23. A process according to claim 1, wherein Steps (1) to (5) are carried out continuously.

24. A process according to claim 1, wherein a compound of formula II is used in which $R_9$ and $R_{10}$ are each independently of the other hydrogen or methyl.

25. A process according to claim 24, wherein a compound of formula II is used in which $R_9$ and $R_{10}$ are hydrogen.

26. A process for the preparation of compounds of formula VII

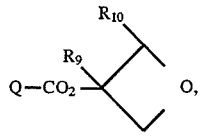
(VII)

wherein Q is a radical of the formula

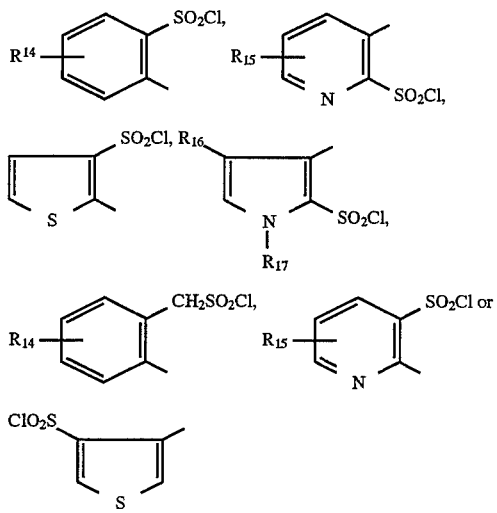

wherein $R_{14}$ is hydrogen, fluorine, chlorine, bromine, iodine or —(X)$_n$$R_3$ wherein X is oxygen, sulfur, SO or SO$_2$, $R_3$ is $C_1$-$C_4$alkyl, $C_1$-$C_4$alkyl substituted by from 1 to 4 halogen atoms, $C_1$-$C_3$alkoxy or by $C_1$-$C_3$alkylthio, or $R_3$ is $C_2$-$C_4$alkenyl or $C_2$-$C_4$alkenyl substituted by from 1 to 4 halogen atoms and n is 0 or 1; or $R_{14}$ is nitro, NR$_4$R$_5$ wherein $R_4$ is hydrogen, methoxy, ethoxy or $C_1$-$C_3$alkyl and $R_5$ is hydrogen or $C_1$-$C_3$alkyl; or $R_{14}$ is —CCR$_6$ wherein $R_6$ is hydrogen, methyl or ethyl; or $R_{14}$ is —O—CHR$_7$—CCR$_6$ wherein $R_6$ is hydrogen, methyl or ethyl and $R_7$ is hydrogen or methyl; or $R_{14}$ is cyano, $R_{15}$ is hydrogen, fluorine, chlorine, $C_1$-$C_4$alkyl or methoxy, $R_{16}$ is hydrogen, fluorine or chlorine and $R_{17}$ is methyl or 2-pyridyl, and $R_9$ and $R_{10}$ are each independently of the other hydrogen or $C_1$-$C_4$alkyl, by reaction of the compound of formula VIII Q-COCl        (VIII), with a 3-hydroxyoxetane of formula I prepared according to the process of claim 1.

27. A process according to claim 26, wherein the 3-hydroxyoxetane of formula I is treated with a bivalent metal salt selected from magnesium or calcium chloride before said 3-hydroxyoxetane is reacted with the compound of formula VIII.

28. A process for the preparation of compounds of formula VIIa

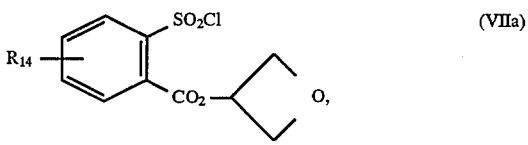
(VIIa)

wherein $R_{14}$ is hydrogen, fluorine, chlorine, bromine, iodine or —(X)$_n$$R_3$ wherein X is oxygen, sulfur, SO or SO$_2$, $R_3$ is $C_1$-$C_4$alkyl, $C_1$-$C_4$alkyl substituted by from 1 to 4 halogen atoms, $C_1$-$C_3$alkoxy or by $C_1$-$C_3$alkylthio, or $R_3$ is $C_2$-$C_4$alkenyl or $C_2$-$C_4$alkenyl substituted by from 1 to 4 halogen atoms and n is 0 or 1; or $R_{14}$ is nitro, NR$_4$R$_5$ wherein $R_4$ is hydrogen, methoxy, ethoxy or $C_1$-$C_3$alkyl and $R_5$ is hydrogen or $C_1$-$C_3$alkyl; or $R_{14}$ is —CCR$_6$ wherein $R_6$ is hydrogen, methyl or ethyl; or $R_{14}$ is —O—CHR$_7$—CCR$_6$ wherein $R_6$ is hydrogen, methyl or ethyl and $R_7$ is hydrogen or methyl; or $R_{14}$ is cyano, by reaction of the compound of formula VIIIa

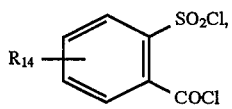 (VIIIa)
wherein $R_{14}$ is as defined, with a 3-hydroxyoxetane of formula I prepared according to the process of claim 1.
29. A process for the preparation of compounds of formula VIIb
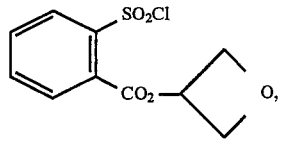 (VIIb)
by reaction of the compound of formula VIIIb
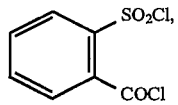 (VIIIb)
with a 3-hydroxyoxetane of formula I prepared according to the process of claim 1.
* * * * *